(12) United States Patent
Pate et al.

(10) Patent No.: US 10,107,744 B2
(45) Date of Patent: Oct. 23, 2018

(54) FREQUENCY HOPPING SPREAD SPECTRUM (FHSS) FOURIER TRANSFORM SPECTROSCOPY

(71) Applicants: University of Virginia Patent Foundation, Charlottesville, VA (US); BrightSpec, Inc., Charlottesville, VA (US)

(72) Inventors: Brooks Hart Pate, Charlottesville, VA (US); Amanda Steber, Mattoon, IL (US); Brent Harris, Charlottesville, VA (US)

(73) Assignees: University of Virginia Patent Foundation, Charlottesville, VA (US); BrightSpec, Inc., Charlottesville, VA (US)

( * ) Notice: Subject to any disclaimer, the term of this patent is extended or adjusted under 35 U.S.C. 154(b) by 0 days.

(21) Appl. No.: 15/319,313

(22) PCT Filed: Jun. 16, 2015

(86) PCT No.: PCT/US2015/035998
§ 371 (c)(1),
(2) Date: Dec. 15, 2016

(87) PCT Pub. No.: WO2015/195641
PCT Pub. Date: Dec. 23, 2015

(65) Prior Publication Data
US 2017/0138847 A1    May 18, 2017

Related U.S. Application Data

(60) Provisional application No. 62/013,165, filed on Jun. 17, 2014.

(51) Int. Cl.
*G01N 21/35* (2014.01)
*G01N 21/3586* (2014.01)

(52) U.S. Cl.
CPC . *G01N 21/3586* (2013.01); *G01N 2021/3595* (2013.01)

(58) Field of Classification Search
CPC .................. G01N 2021/3595; G01N 21/3586
See application file for complete search history.

(56) References Cited

U.S. PATENT DOCUMENTS 3,968,424 A    7/1976  Ernst
4,677,852 A    7/1987  Pinyan
(Continued)

FOREIGN PATENT DOCUMENTS

JP    2017520004 A    7/2017
WO    WO-2012129089 A1    9/2012
(Continued)

OTHER PUBLICATIONS

"European Application No. 15809685.9, Response filed Aug. 28, 2017 to Response to Communication pursuant to Rules 161(2) and 162 EPC dated Jun. 12, 2017", 18 pgs.
(Continued)

*Primary Examiner* — Marcus Taningco
(74) *Attorney, Agent, or Firm* — Schwegman Lundberg & Woessner, P.A.

(57) ABSTRACT

Apparatus and techniques for broadband Fourier transform spectroscopy can include frequency hopping spread-spectrum spectroscopy approaches. For example, an excitation source power can be spread over a specified frequency bandwidth, such as by applying a sequence of short, transform-limited pulses to a sample. Each pulse can include a specified carrier frequency, and a corresponding bandwidth of the individual pulse can be determined by a frequency domain representation when Fourier transformed. A series of short excitation pulses can be used to create an excitation sequence, such as to deliver a specified or desired amount of (Continued)

power to the sample, such as by having the excitation source enabled for a time comparable to a free induction decay (FID) dephasing time.

19 Claims, 11 Drawing Sheets

(56) References Cited

U.S. PATENT DOCUMENTS

| | | | | |
|---|---|---|---|---|
| 4,766,377 | A | * | 8/1988 | Ohuchi .............. G01R 33/4633 324/307 |
| 5,949,291 | A | | 9/1999 | Newland |
| 7,342,229 | B1 | | 3/2008 | Reiss |
| 8,748,822 | B1 | | 6/2014 | Gerecht et al. |
| 2003/0038935 | A1 | | 2/2003 | Pan et al. |
| 2005/0105099 | A1 | | 5/2005 | Shpantzer et al. |
| 2013/0154611 | A1 | | 6/2013 | Pate et al. |
| 2013/0265573 | A1 | | 10/2013 | Pate et al. |
| 2016/0131600 | A1 | * | 5/2016 | Pate ....................... G01N 22/00 250/339.08 |

FOREIGN PATENT DOCUMENTS

| | | |
|---|---|---|
| WO | WO-2015195641 A2 | 12/2015 |
| WO | WO-2015195641 A3 | 12/2015 |

OTHER PUBLICATIONS

"International Application Serial No. PCT/US2015/035998, International Preliminary Report on Patentability dated Dec. 29, 2016", 10 pgs.
"International Application Serial No. PCT/US2015/035998, International Search Report dated Jan. 11, 2016", 4 pgs.
"International Application Serial No. PCT/US2015/035998, Invitation to Pay Additional Fees and Partial Search Report dated Aug. 17, 2015", 2 pgs.
"International Application Serial No. PCT/US2015/035998, Written Opinion dated Jan. 11, 2016", 8 pgs.
Balle, T. J, et al., "Fabry—Perot cavity pulsed Fourier transform microwave spectrometer with a pulsed nozzle particle source", Rev. Sci. Instrum., 52, (1981), 33-45.
Brown, G. G, et al., "A broadband Fourier transform microwave spectrometer based on chirped pulse excitation", Rev Sci Instrum., 79(5), American Institute of Physics, (May 2008), 053103-1-053103-13.
Brown, Gordon, et al., "The rotational spectrum of epifluorohydrin measured by chirped-pulse Fourier transform microwave spectroscopy", Journal of Molecular Spectroscopy, 238(2), (Aug. 2006), 200-212.
Coddington, Ian, et al., "Time-domain spectroscopy of molecular free-induction decay in the infrared", Optics Letters, vol. 35, No. 9, (2010), 1395-1397.
Dian, Brian C., et al., "Seeing Is Believing: An 11 GHz molecular beam rotational spectrum (7.5-18.5 GHz) with 100 kHz resolution in 15 us measurement time", International Symposium on Molecular Spectroscopy, (Jun. 20, 2005), 29 pgs.
Douglass, K. O, et al., "Progress towards chirped-pulse Fourier transform THz spectroscopy", 64th International Symposium on Molecular Spectroscopy, Columbus, OH, [Online]. Retrieved from the Internet: <URL: http://hdl.handle.net/1811/46369>, (Jun. 21-25, 2010), 21 pgs.
Ekkers, J., et al., "Pulsed microwave Fourier transform spectrometer", Rev. Sci. Instrum., 47, (1976), 448-454.
Finneran, I. A, et al., "A direct digital synthesis chirped pulse Fourier transform microwave spectrometer", Rev Sci Instrum., 84(8), (Aug. 2013), 083104.
Gerecht, E., et al., "Chirped-pulse terahertz spectroscopy for broadband trace gas sensing", Opt Express., 19(9), (Apr. 25, 2011), 8973-84.
Gerecht, Eyal, et al., "Chirped-Pulse Terahertz Spectroscopy for Broadband Tracegas Sensing", National Institute of Standards and Technology, Optical Technology Division, (Jun. 21, 2011), 24 pgs.
Gerecht, Eyal, et al., "Recent Progress in Chirped-Pulse Fourier Transform THz Spectroscopy", NIST, (Jun. 23, 2010), 20 pgs.
Gerecht, Eyal, "Recent Progress in Chirped-Pulse Fourier Transform THz spectroscopy (with embedded notes)", NIST, (Apr. 19, 2016), 40 pgs.
Kuyanov-Prozument, K., et al., "Direct Observation of Rydberg—Rydberg Transitions in Calcium Atoms", International Symposium on Molecular Spectroscopy, (Jun. 22, 2010), 20 pgs.
Lesarri, Alberto, et al., "Interplay of Phenol and Isopropyl Isomerism in Propofol from Broadband Chirped-Pulse Microwave Spectroscopy", American Chemical Society, vol. 132, No. 38, (Sep. 7, 2010), 13417-13424.
Medvedev, I. R, et al., "Chemical analysis in the submillimetre spectral region with a compact solid state system", Analyst, 131(12), (Dec. 2006), 1299-307.
Neese, C. F, et al., "Compact Submillimeter/Terahertz Gas Sensor With Efficient Gas Collection, Preconcentration, and ppt Sensitivity", IEEE Sensors Journal, 12(8), (Aug. 2012), 2565-2574.
Neill, Justin L., et al., "Next generation techniques in the high resolution spectroscopy of biologically relevant molecules", Phys. Chem. Chem. Phys.,13, (2011), 7253-7262.
Neill, Justin L., et al., "Rotational spectroscopy of iodobenzene and iodobenzene—neon with a direct digital 2-8 GHz chirped-pulse Fourier transform microwave spectrometer", Journal of Molecular Spectroscopy, (2011), 21-29.
Neill, Justin L, et al., "Segmented chirped-pulse Fourier transform submillimeter spectroscopy for broadband gas analysis", Optics Express, 21(17), (2013), 19743-19749.
Neill, Justin L., et al., "Techniques for High-Bandwidth (> 30 GHz) Chirped-Pulse Millimeter/Submillimeter Spectroscopy", (Jun. 23, 2011), 22 pgs.
Park, Barratt G, et al., "Design and evaluation of a pulsed-jet chirped-pulse milimeter-wave spectrometer for the 70-102 GHz region", AIP the Journal of Chemical Physics 135, 024202, (2011), 1-10.
Park, G. B, et al., "Design and chemical application of chirped-pulse millimeter-wave spectroscopy", 64th International Symposium on Molecular Spectroscopy, Columbus, OH [Online]. Retrieved from the Internet: <URL: http://hdl.handle.net/1811/38114 >, (41 pgs), Jun. 22-26, 2009.
Park, G. Barratt, et al., "Design and evaluation of a pulsed-jet chirped-pulse millimeter-wave spectrometer for the 70-102 GHz region", AIP the Journal of Chemical Physics 135, 024202, (2011), 1-10.
Prozument, Kirill, "Chirped-Pulse Millimeter-Wave Spectroscopy of Rydberg-Rydberg Transitions", American Physical Society, (2011), 5 pgs.
Shipman, Steven T., et al., "Design and performance of a direct digital chirped-pulse Fourier transform microwave (CP-FTMW) spectrometer operating from 2-8 GHz", International Symposium on Molecular Spectroscopy, (Jun. 18, 2008), 29 pgs.
Shipman, Steven, et al., "Waveguide Chirped-Pulse FTMW Spectroscopy", (Jun. 18, 2008), 29 pgs.
Spokas, J. J, et al., "Nuclear Relaxation in Aluminum", Phys. Rev., 113 (Mar. 15, 1959), 1462.
Steber, Amanda L, et al., "An arbitrary waveform generator based chirped pulse Fourier transform spectrometer operating from 260 to 295 GHz", Journal of Molecular Spectroscopy, 280, (3-10), Oct. 2012.
Twagirayezu, Sylvestre, "Vibrational Coupling Pathways in Methanol as Revealed by Coherence-Converted Population Transfer Fourier Transform Microwave Infrared Double-Resonance Spectroscopy", J. Phys. Chem. A, vol. 114, No. 25, (2010), 6818-6828.
Zaleski, Daniel P., et al., "A Ka-Band Chirped-Pulse Fourier Transform Microwave Spectrometer", International Symposium on Molecular Spectroscopy, (Jun. 22, 2010), 17 pgs.
Zaleski, Daniel, et al., "A Ka-band chirped-pulse Fourier transform microwave spectrometer", Article in Journal of Molecular Spectroscopy, (Oct. 2012), 10 pgs.

(56) References Cited

OTHER PUBLICATIONS

"European Application Serial No. 15809685.9, Extended European Search Report dated Feb. 7, 2018", 9 pgs.

James, Keeler, "4 Fourier transformation and data processing", [Online] Retrieved from the Internet : <http://www-keeler.ch.cam.ac.uk/lectures/understanding/chapter.©.pdf>, (Mar. 1, 2004).

Smith, Albert A, et al., "A 140GHz pulsed EPR/212MHz NMR spectrometer for DNP studies", Journal of Magnetic Resonance, vol. 223, (Jul. 20, 2012), 170-179.

* cited by examiner

FREQUENCY HOPPING SPREAD SPECTRUM (FHSS) FOURIER TRANSFORM SPECTROSCOPY

CLAIM OF PRIORITY

This patent application is a U.S. National Stage Filing under 35 U.S.C. 371 from International Application No. PCT/US2015/035998, filed on Jun. 16, 2015, and published as WO 2015/195641 on Dec. 23, 2015, which claims the benefit of priority of Pate et al., U.S. Provisional Patent Application Ser. No. 62/013,165, titled "FREQUENCY HOPPING SPREAD SPECTRUM (FHSS) FOURIER TRANSFORM SPECTROSCOPY," which was filed on Jun. 17, 2014, and which are incorporated herein by reference in their entireties.

STATEMENT REGARDING FEDERALLY SPONSORED RESEARCH OR DEVELOPMENT

This invention was made with government support under SBIR Topic A13-007 awarded by the United States Army and under Chemistry Award 1213200 awarded by the National Science Foundation. The government has certain rights in the invention.

BACKGROUND

Molecular rotational spectroscopy is a technique that offers high chemical selectivity and sensitivity and can be used to analyze gas samples, such as mixtures. Techniques for broadband spectroscopy, especially in the field of molecular rotational spectroscopy, offer significant improvements in measurement time and detection sensitivity as compared to other approaches. For room-temperature samples, a peak of the spectral intensity of a rotational spectrum typically occurs in the range of millimeter-wave ("mm-wave") frequencies (e.g., from about 60 gigahertz (GHz) to about 1000 GHz), particularly for molecules with 2-10 "heavy" nuclei (non-hydrogen atoms). A molecular rotational spectrum of most molecules will contain multiple, spectrally narrow transitions in any fixed mm-wave frequency range of modest bandwidth (e.g., a bandwidth of about 30 to about 50 GHz). Broadband techniques can be useful in cases where the power available from light sources exceeds a threshold to saturate the molecular transitions. For rotational spectroscopy of low pressure gases (such as in molecular beams or static gases) the power meeting a threshold for saturation is often orders of magnitude lower than the power provided by generally-available microwave-to-terahertz (THz) light sources.

OVERVIEW

Apparatus and techniques for broadband Fourier transform spectroscopy can include frequency-hopping spread-spectrum spectroscopy approaches. For example, an excitation source power can be spread over a specified frequency bandwidth, such as by applying a sequence of short, transform-limited pulses to a sample. Each pulse can include a specified carrier frequency, and a corresponding bandwidth of the individual pulse can be determined by a frequency domain representation when Fourier transformed. A series of short excitation pulses can be used to create an excitation sequence, such as to deliver a specified or desired amount of power to the sample, such as by having the excitation source enabled for a time comparable to a free induction decay (FID) dephasing time. An advantage of the frequency hopping approach is that high quality microwave light sources (e.g., as used for microwave spectroscopy and for light generation at mm-wave/THz frequencies when active multiplier chain technology is used) are generally available as MMIC packages at exceptionally low cost.

In an example, an apparatus can include a signal generator circuit (such as a pattern generator circuit) configured to output a pulse sequence, the pulse sequence including durations during which frequencies selected from a first frequency range are output, including at least three different frequencies output serially within the pulse sequence, a frequency multiplier circuit operably coupled to the pattern generator circuit and configured to upconvert the pulse sequence to an upconverted pulse sequence having a higher second range of frequencies beyond the first range of frequencies, a sample cell in electromagnetic communication with coupled to the frequency multiplier circuit and configured to receive the upconverted pulse sequence as an excitation to a sample, and an analog-to-digital converter configured to acquire a digital representation of an output from the sample cell elicited in response to the upconverted pulse sequence.

In an example, a technique such as a method can include performing millimeter wave spectroscopy on a sample, including generating a pulse sequence comprising a count, N, of different frequencies and a count, M, of unique permutations of the order in which the count N of different frequencies are output, applying the pulse sequence to the sample so as to elicit a response from the sample, acquiring a time-domain representation of the response; and forming a frequency-domain representation of the time-domain representation.

In an example, an apparatus for performing millimeter-wave spectroscopy of a sample can include a signal generator to generate a frequency-hopping excitation signal, the frequency-hopping excitation signal having a duration, T, and a bandwidth of about N/T, wherein the duration T is less than a dephasing time of the sample and N>2 is the number of frequencies in the frequency-hopping excitation signal, a sample holder, in electromagnetic communication with the signal generator, to apply the frequency-hopping excitation signal to the sample so as to produce a response from the sample, a mixer, in electromagnetic communication with the sample holder, to mix the response with a local oscillator so as to produce an analog representation of the response, and an analog-to-digital converter (ADC), operably coupled to the mixer, to generate a digital representation of the response based on the an analog representation of the response.

In an example, a technique such as a method of performing millimeter-wave spectroscopy of a sample can include generating a frequency-hopping excitation signal, the frequency-hopping excitation signal having a duration, T, and a bandwidth of about N/T, wherein the duration T is less than a dephasing time of the sample and N>2 is the number of frequencies in the frequency-hopping excitation signal, applying the frequency-hopping excitation signal to the sample so as to produce a response from the sample, detecting an analog representation of the response, and generating a digital representation of the response based on the an analog representation of the response.

This overview is intended to provide an overview of subject matter of the present patent application. It is not intended to provide an exclusive or exhaustive explanation of the invention. The detailed description is included to provide further information about the present patent application.

Figure 1:
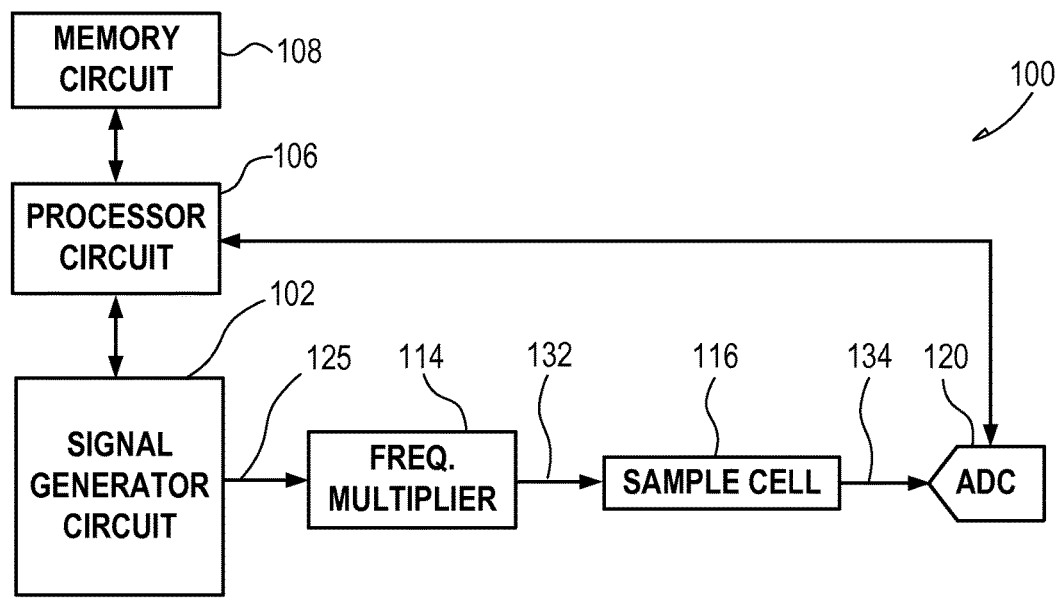
FIG. 1 illustrates generally an example that can include at least a portion of a system operable to perform a Frequency Hopping Spread Spectrum (FHSS) spectroscopy technique.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

In one approach for performing molecular spectroscopy, to avoid saturation of molecular transitions, a power from an excitation source (e.g., a "light" source) can be spread over a specified frequency bandwidth—an approach that can be referred to as "spread spectrum" in signal processing. Accordingly, a total output power can remain high, but a power density versus frequency is correspondingly reduced due to spreading of the energy over a range of frequencies. A chirped-pulse Fourier transform spectroscopy approach can be used for microwave and millimeter wavelength (mm-wave or terahertz (THz)) molecular rotational spectroscopy. A chirped-pulse technique generally uses a "chirp spread spectrum" approach to spread the power density over a large-enough spectral bandwidth to avoid saturation effects. Increased measurement sensitivity can be gained by making Fourier transform spectroscopy measurements where a coherent emission from the macroscopic polarization of the sample is detected. Detection of a coherent emission (e.g., "free induction decay" (FID)) signal is generally background-free so that noise in the light excitation source is not detected. Generally, Fourier transform approaches include a time duration of the excitation source that is shorter than (but on the order of) the dephasing time of the coherent FID. This dephasing time can be caused by inhomogeneous effects, like the dephasing associated with a Doppler spread of molecular spectroscopy frequencies, or by homogeneous effects including molecular collisions in the gas sample.

As mentioned above, a chirped pulse is a useful pulse shape for "spread spectrum" Fourier transform spectroscopy. The chirped pulse shape separates the excitation bandwidth from the pulse duration. Such bandwidth and duration quantities are generally inversely related in more traditional "transform limited" pulse shapes. Therefore, using a chirped pulse approach, excitation bandwidth and pulse duration can be independently selected (e.g., where the pulse duration is selected to be a time on the order of the dephasing time to achieve a desired signal-to-noise ratio in the measurement cycle). However, the creation of phase-stable chirped pulses (e.g., permitting time-domain signal averaging for use in Fourier transform measurements) generally includes use of high-cost arbitrary waveform generators. In another approach, direct digital synthesis (DDS) monolithic microwave integrated circuits (MMICs) can be used in chirped-pulse spectrometer apparatus.

The present subject matter includes apparatus and techniques for broadband Fourier transform spectroscopy that can include frequency hopping spread spectroscopy approaches. In this manner, an excitation source power can be spread over a specified frequency bandwidth, such as by applying a sequence of short, transform-limited pulses to a sample. Each pulse can include its own carrier frequency and a corresponding bandwidth of the individual pulse can be determined by its frequency domain representation when Fourier transformed. By using a series of short excitation pulses to create a full excitation sequence it is possible to deliver a specified or desired amount of power to the sample, such as by having the excitation source enabled for a time comparable to the FID dephasing time, but without requiring use of costly arbitrary waveform generators as in the chirped-pulse approach.

FIG. 1 illustrates generally an example that can include at least a portion of a system 100 operable to perform a Frequency Hopping Spread Spectrum (FHSS) spectroscopy technique. A signal generator circuit 102 can be operably coupled to a frequency multiplier 114, such as including an active multiplier chain. An output of the frequency multiplier 114 can be arranged in electromagnetic communication with a sample cell 116. The signal generator 102 can include a pattern generator circuit as shown and described elsewhere herein, such as including one or more digitally-controlled synthesizers or oscillators.

The sample cell 116 can include a chamber or free-space cell configuration, such as having an electromagnetic emitter (e.g., a horn antenna or other coupling configuration) located at a source location, such as electromagnetically coupled to an output of the frequency multiplier 114. An electromagnetic receiver can be included at another location within or nearby the sample cell 116, such as to provide an output 134. The output 134 can carry an analog representation of a signal elicited from a gas-phase sample located in the sample cell 116, such as in response to excitation provided by the signal generator circuit 102 and frequency multiplier 114.

The signal provided at the output 134 can be further processed, such as downconverted as shown in other examples described herein, and a digital representation of the signal can be provided such as using an analog-to-digital converter 120 (e.g., a digitizer). The digital representation can be further processed in the digital domain, such as using a processor circuit 106 and memory circuit 108, such as can include instructions to transform a time-domain digital representation of the signal from the output 134 to a frequency-domain representation, or to perform other techniques as shown and described elsewhere herein. For example, a discrete Fourier transform such as a Fast Fourier Transform (FFT) can be performed on a digital representation of a time-domain analog signal. If FHSS excitation is used, a combined FHSS and Fourier transform technique can be referred to as FHSS-FT spectroscopy. The processor circuit can be coupled to the signal generator circuit 102 or other portions of the system 100, such as to at least partially automate operation of the system 100 for performing an FHSS-FT spectroscopy technique.

Figure 2:
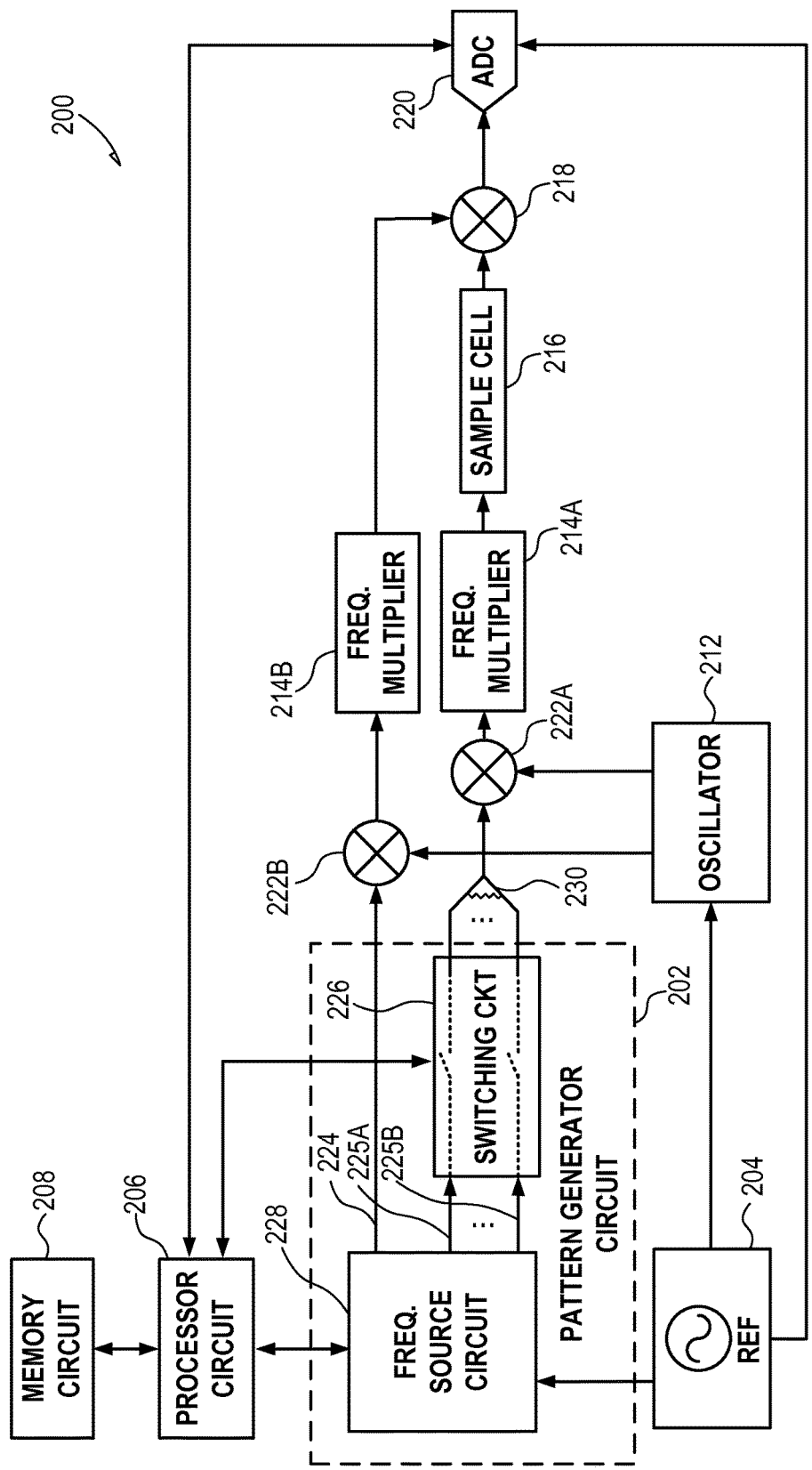
FIG. 2 illustrates generally an example that can include at least a portion of a system operable to perform an FHSS spectroscopy technique, and such as can include one or more mixers.

FIG. 2 illustrates generally an example that can include at least a portion of a system 200 operable to perform an FHSS spectroscopy technique, and such as can include one or more mixers. The system 200 can include a pattern generator circuit 202, such as including a frequency source circuit 228 (e.g., including one or more digitally-controlled synthesizers or other sources as described in relation to other examples herein). The frequency source circuit 228 can include multiple outputs, such as first and second frequency outputs 225A and 225B, such as can be routed to a switching circuit 226. The switching circuit 226 can be controlled to provide a time-sequence of excitation frequency pulses, such as can be combined using a power combiner 230 or using other techniques. The combined output from the power combiner 230 can be operably coupled to a first upconversion mixer 222A. The first upconversion mixer can mix the excitation frequency pulses from the pattern generator circuit 202 with a local oscillator (LO) frequency provided by an oscillator 212 (or, for example, provided by another output from the frequency source circuit 228). An upconverted output of the first mixer circuit 222A can be operably coupled to a first frequency multiplier 214A (e.g., an active multiplier chain). An output of the first frequency multiplier 214A can be arranged in electromagnetic communication with a sample cell 216, as mentioned in relation to the example of FIG. 1, above.

An output of the sample cell 216 can be arranged in electromagnetic communication with a downconversion mixer 218, such as to provide an output signal within the bandwidth of an analog-to-digital converter 220. A downconversion local oscillator frequency can be provided, such as using a second frequency multiplier 214B operably coupled to an output of a second upconversion mixer 222B. The oscillator 212 can also provide an LO frequency for the second upconversion mixer 222B. The downconversion mixer 218 local oscillator frequency can be established at least in part such as using a frequency source output 224 provided by the frequency source circuit 228, such as by mixing the frequency source output 224 with an LO frequency from the oscillator 212 and then frequency multiplying the resulting upconverted output from the second upconversion mixer 222B using the second frequency multiplier 214B. In this manner, the frequency source circuit can be configured to provide outputs, for example, in a microwave range of frequencies, and a sample located in the sample cell region can be excited or probed according to an FHSS spectroscopy technique using a much higher range of frequencies such as in the millimeter-wave or terahertz (THz) range of frequencies. As in the example of FIG. 1, one or more portions of the system 200 shown in FIG. 2 can be operably coupled to a processor circuit 206, such as to perform processing in the digital domain or to at least partially automate a spectroscopy protocol. Phase-coherent measurements can be performed at least in part by locking one or more portions of the system 200 to a frequency reference 204 (e.g., a reference oscillator such as including a frequency reference derived from a molecular energy level transition).

Figure 3:
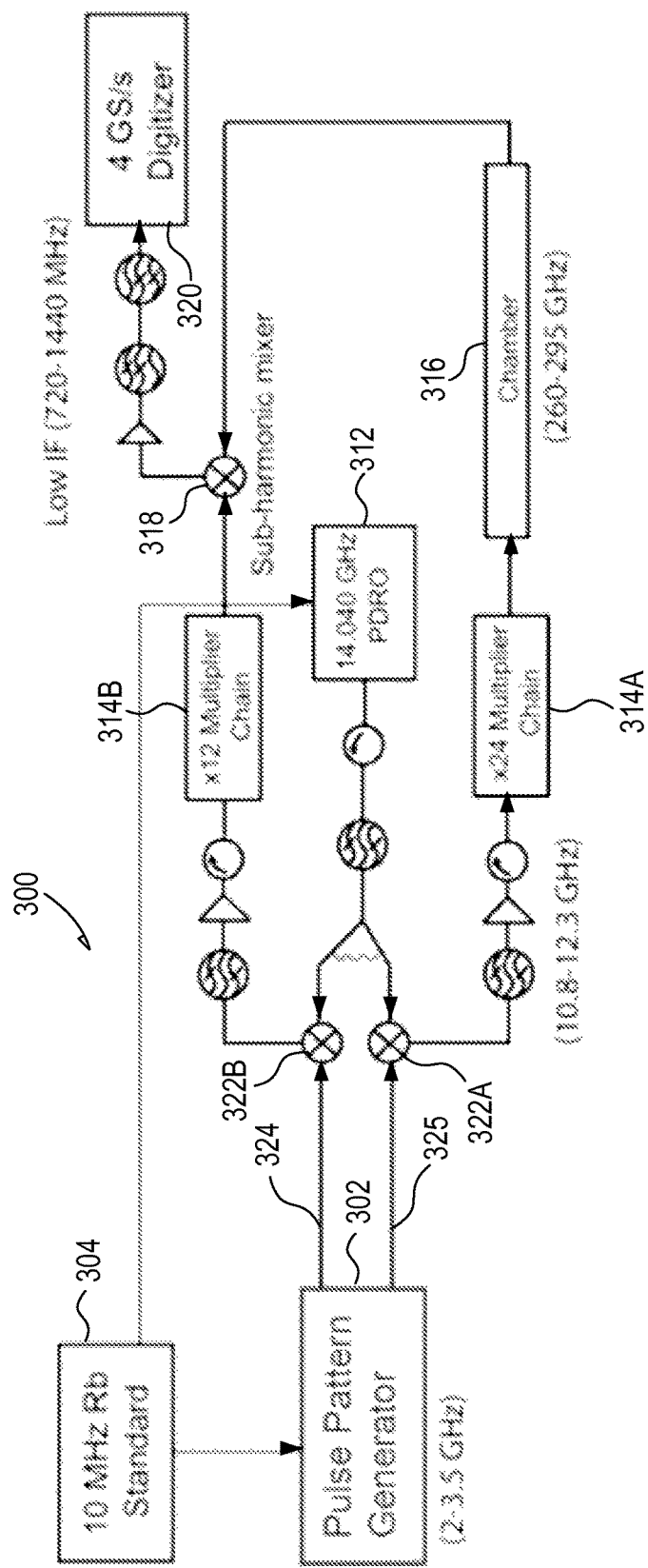
FIG. 3 illustrates generally an illustrative example that can include at least a portion of a system operable to perform an FHSS spectroscopy technique, such as to excite or probe a sample in a frequency range from about 260 gigahertz (GHz) to about 295 GHz.

FIG. 3 illustrates generally an illustrative example that can include at least a portion of a system 300 that can be used to perform an FHSS spectroscopy technique, such as to excite or probe a sample in a frequency range from about 260 gigahertz (GHz) to about 295 GHz (e.g., within a "millimeter-wave" or "mm-wave" range of wavelengths). The system 300 can include a first active multiplier chain (AMC) 314A that takes a microwave input frequency and multiplies the input frequency into the mm-wave frequency range. In this illustrative example, a factor of 24 multiplication can be used to reach 260-295 GHz, such as derived from a microwave input from about 10.833 to about 12.083 GHz.

In this example, a microwave input frequency range is higher than is available for certain generally-available commodity integrated circuit (IC) microwave synthesizers. Accordingly, a frequency upconversion circuit with a single-frequency microwave source can be used to provide an input to the AMC 314A. For example, a pulse pattern generator circuit can be used to provide a sequence of output frequencies at an output 325. The output 325 can be operably coupled to a first upconversion mixer 322A, such as having a local oscillator (LO) input provided at least in part using a phase-locked dielectric resonator oscillator (PDRO) 312 or provided using other source. An output of the first upconversion mixer 322A can be further processed such as using one or more amplifiers, filters, or circulators, and the output can be operably coupled to the first AMC 314A. An output of the first AMC 314A can include a frequency-multiplied representation of a sequence of pulses having different frequencies, and the pulse sequence can be provided to excite or probe a sample located in a chamber 316 or other sample holder.

A signal elicited in response to one or more of an excitation sequence or probe energy can be detected, such as by digitizing an output derived from the chamber 316. For example, a coherent free induction decay (FID) from the sample can be detected using a sub-harmonic mixer 318 and a local oscillator (LO) can be provided at least in part using an output 324 provided by a synthesizer IC, such as included as a portion of a pulse pattern generator circuit 302. An output from the sub-harmonic mixer 318 can be within a digitization bandwidth of a high-speed digitizer (e.g., a 4 gigasample per second (GS/s) digitizder 320 as shown illustratively in FIG. 3).

An LO signal for the subharmonic mixer 318 may also be outside a range that can be generated directly using a microwave synthesizer. Accordingly, a second upconversion mixer 322B can be used, such as to upconvert the output 324 from the pulse pattern generator circuit 302. As in the example of the first upconversion mixer 322A, a local oscillator for the second upconversion mixer 322B can be provided at least in part using the PDRO 312. An output of the second upconversion mixer 322B can be coupled to a second multiplier chain (e.g., a second AMC 314B), and the output of the AMC 314B can be operably coupled to the sub-harmonic mixer 318 to provide a local oscillator for the sub-harmonic mixer 318.

To achieve stability and maintain phase-coherenence, a frequency reference such as a 10 megahertz (MHz) rubidium (Rb) standard 304 can be used, such as operably coupled to one or more other portions of the system 300 such as the pulse pattern generator 302 or the PDRO 312. The illustrative example of FIG. 3 shows a system that can be used to perform FHSS spectroscopy in a frequency range from about 260 to about 295 gigahertz (GHz). Such a range is generally suitable for the analysis of room-temperature gases by molecular rotational spectroscopy. However, other examples can include spectrometers configured to operate in another, different frequency range, such as specified from within the microwave through THz frequency ranges.

Figure 4:
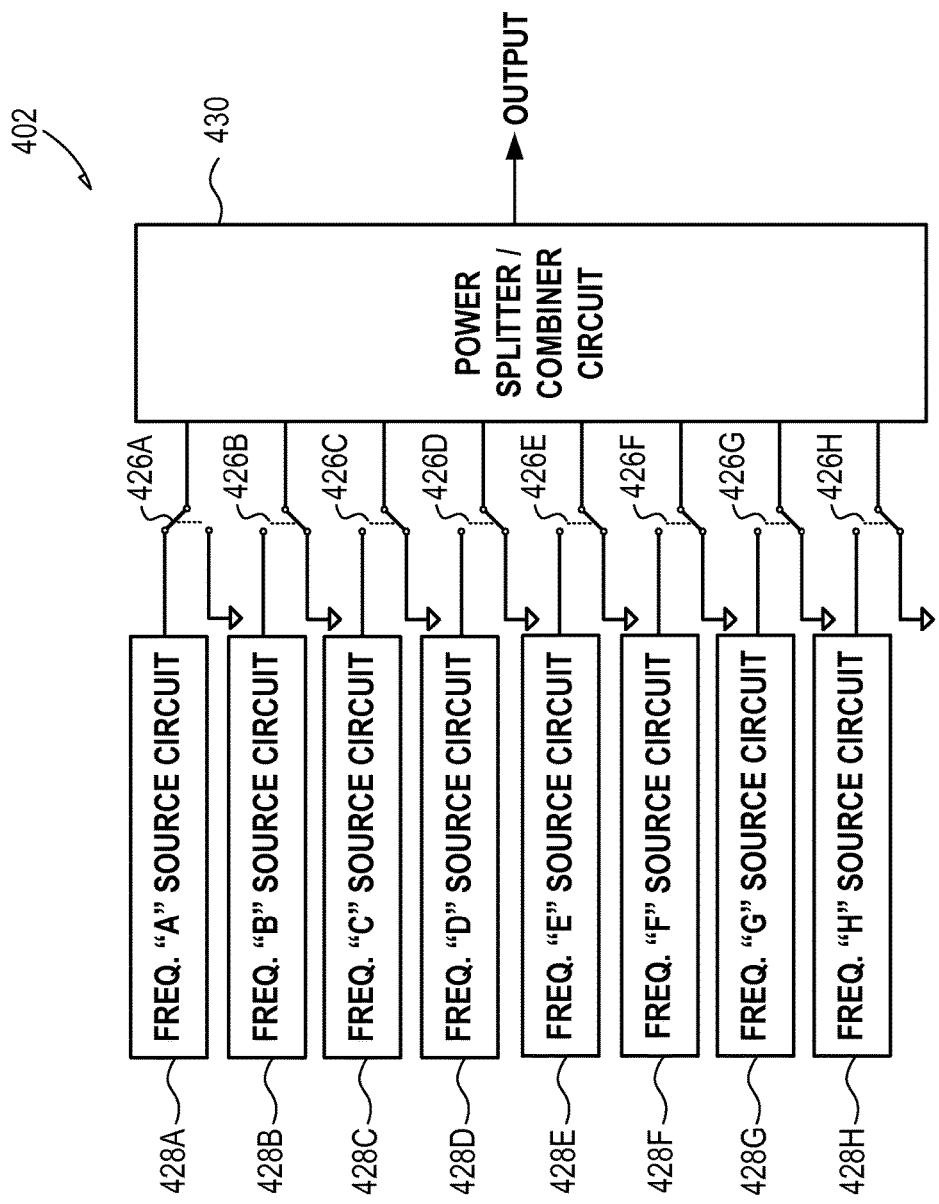
FIG. 4 illustrates generally an illustrative example of a pattern generator circuit, such as can include respective frequency source circuits, switching circuits, and a combiner circuit.

Various arrangements can be used to provide a pulse pattern generator circuit or other signal generator circuit. For example, respective frequency source circuits can be configured to independently provide different microwave frequencies. For example, an individual output can be configured to provide one or more output frequencies, or a switch can be used to select amongst an array of fixed-frequency outputs. For example, FIG. 4 illustrates generally an illustrative example of a pulse pattern generator circuit, such as can include respective frequency source circuits 428A through 428H, switching circuits 426A through 426H, and a combiner circuit 430. The pulse pattern generator circuit, or other similar circuit topologies, can be used in relation to other examples described herein, such as to provide a signal source for performing an FHSS spectroscopy technique. For example, the frequency source circuits 428A through 428H can include one or more wideband microwave synthesizer integrated circuits (ICs) to provide one or more of digitally-controlled or programmable frequency sources (e.g., to output respective output frequencies, "A" through "H," in an example having 8 output channels). In another example, a direct digital synthesis (DDS) IC could provide several frequencies such as selected or enabled through a corresponding set of digital control lines. In the example of FIG. 4, each single-pole, double-throw (SPDT) switch 426A through 426H can be controlled by a separate digital signal line. In the switch state shown illustratively in FIG. 4, only frequency "A" from frequency source circuit 426A is output from the circuit 402.

In an example, the switching circuits 426A through 426H can include high-speed microwave switches, such as attached to the output of each respective frequency source circuit 428A through 428H. In the illustration of FIG. 4, eight digital control lines from a digital pattern generator can be used to control the switching circuits 428A through 428H. For example, a Byte Paradigm Wave Gen Xpress (Byte Paradigm sprl, Belgium) has been used to provide the experimentally obtained measurement results shown and described elsewhere herein. In the FHSS-FT spectroscopy technique, only one "color" (e.g., a pulsed output having a specified center frequency) is applied to the sample at a time. Therefore, in an example where eight frequency outputs are available, a total of nine digital patterns are used to control the microwave generator: 00000000 (all off), 10000000 (e.g., color "A" on), 01000000 (e.g., color "B" on) . . . 00000001 (e.g., color "C" on). A power combiner 430 can be used to create a single output from the bank of pulse-controlled microwave generators. Such an output can be upconverted and amplified for delivery to the sample cell. In one approach, a pulse duration of one or more microwave pulses can be determined using the digital pattern generator circuit. For example, the digital pattern generator can include a digital pattern buffer having 10 nanosecond (ns) time resolution (e.g., using a 100 MHz clock), such as selected to exceed or be comparable to the settling time or latency of the high-speed microwave switches. By selectively enabling a switch for a desired pulse duration, square pulses with durations of 10 ns, 20 ns, 30 ns, or other durations can be generated. Multiple microwave pulse pattern generators circuits can be used to further increase the numbers of colors (e.g., frequencies) available while still keeping system costs modest.

The frequency-hopping technique can also be implemented using direct digital synthesizers (DDS). For example, the AD9914 DDS chip from Analog Devices (Norwood, Mass., USA), can be programmed for eight independent frequencies. The output frequency at a given time is specified by a control line with 3 binary inputs (for $2^3=8$ distinct output states). FHSS spectroscopy also generally involves an "off" state (because the frequency source is quiet during the molecular FID measurement). There are at least two techniques that can be used to provide an "off" state while still providing acceptable noise and distortion characteristics. In a first example, a high speed PIN diode switch can be used that uses a control line to specify whether the output of the DDS circuit is enabled or disabled (e.g., by gating the output of the DDS circuit using the PIN diode). In this first illustrative example, a total of four control channels can be used to select a total of eight frequencies.

In a second illustrative example, one of the eight DDS outputs can be programmed to a frequency well below the others (for example, 1 MHz as compared to other frequencies in the microwave range). A high-pass filter can be placed on the output of the DDS chip, and the filter can absorb or reflect (e.g., reject) the 1 MHz output but can allow transmission of the other seven output frequencies for use in excitation or probing of a sample. The very-low-frequency output can be selected in the DDS binary control when the "off" state is desired. The second illustrative example can yield more tunable colors per control line (e.g., 7 frequencies, plus an "off" state, can be chosen using 3 binary control lines) and a cleaner output.

Experimentally-obtained measurements of molecular rotational spectra using the 260-295 GHz mm-wave rotational spectroscopy apparatus of FIG. 3 have been performed, but using an arbitrary waveform generator (AWG) to serve as a microwave pulse pattern generator circuit. In such measurements, the typical free induction decay (FID) dephasing time is about 500 ns and is attributed to Doppler dephasing. Therefore, a total time duration of the pulse pattern (including each of the excitation "colors") can be selected to be on this order. For example, a total excitation duration of about 200 ns has been used to provide the experimentally-obtained results herein (e.g., comprising several shorter individual frequency pulses). In this manner, the source power can be spread over a larger bandwidth by using a series of shorter time pulses. The prototype measurements have used individual pulses with duration of 40 ns giving a bandwidth of about 25 MHz for each pulse. By contrast, if a single, square pulse of duration 200 ns is employed, then the source power is spread over a bandwidth of only about 5 MHz and, in fact, this narrow spread of power can cause nonlinear excitation (e.g., saturation) with the available source power in many cases.

As mentioned above, an advantage of the frequency hopping approach is that high quality microwave light sources (e.g., as used for microwave spectroscopy and for light generation at mm-wave/THz frequencies when active multiplier chain technology is used) are generally available as MMIC packages at exceptionally low cost. As another illustrative example, a wideband microwave synthesizer MMIC, such as the AD4350 or ADF4351 series from Analog Devices (Norwood, Mass., USA), or the MAX2870 series from Maxim Integrated Products (San Jose, Calif., USA), can be used in FHSS-Fourier transform spectrometers as the frequency source circuits at a modest cost of a few dollars per device for such generally-available components. As another illustrative example, the pulse generation used for the FHSS-Fourier transform technique can also be achieved using one or more DDS circuits, such as the AD9914 series from Analog Devices, which can offer a subset of programmed frequencies selectable through digital control lines.

In addition to the lower cost of integrated frequency sources as compared to an arbitrary waveform generator, such integrated sources can offer better performance as compared to other approaches. Any spurious content from the frequency source leads to spurious signals that appear on the detector (e.g., an analog-to-digital converter) and such spurious signals may then need to be removed from the spectrum, such as resulting in a poorer signal-to-noise ratio. Synthesizers are available that have approximately a factor of 100 less power in spurious content than the best presently-available arbitrary waveform generators. Use of such synthesizers can thereby lead to a reduced electronic background spectrum against which molecular emission signals are detected, as compared to other approaches.

Additionally, generally-available arbitrary waveform generators that can be used for broadband millimeter wave spectroscopy can generally only provide signal having an upper frequency limit of about 3.9 GHz. One or more of frequency upconversion or multiplication can then used to bring these signals up to the input frequency range (typically between 10-18 GHz) for the millimeter wave active multiplier chains. Upconversion and multiplication can add cost or complexity, and can decrease reliability, such as by introducing failure points, and can introduce additional spurious and noise content. Wideband tunable synthesizers are increasingly available at higher frequencies, most recently the ADF5355 from Analog Devices that covers from 0.05-13.6 GHz. With higher frequency synthesizers, spectrometers can be built that greatly simplify this upconversion/pre-multiplication stage, giving the cleanest possible sources for high sensitivity millimeter wave spectroscopy.

Figure 5A:
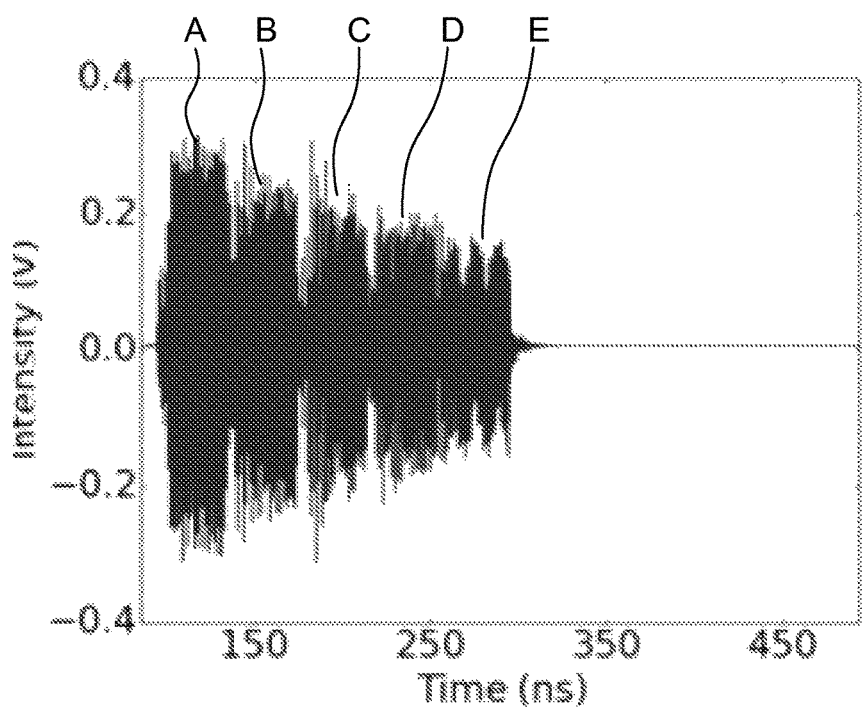
FIGS. 5A and 5B illustrate generally time-domain intensity plots of two illustrative permutations of an excitation sequence, where similar frequencies can be used in each of the sequences shown in FIGS. 5A and 5B, but where the order of the delivered frequencies is varied between the permutations shown in FIG. 5A and FIG. 5B.
Figure 5B:
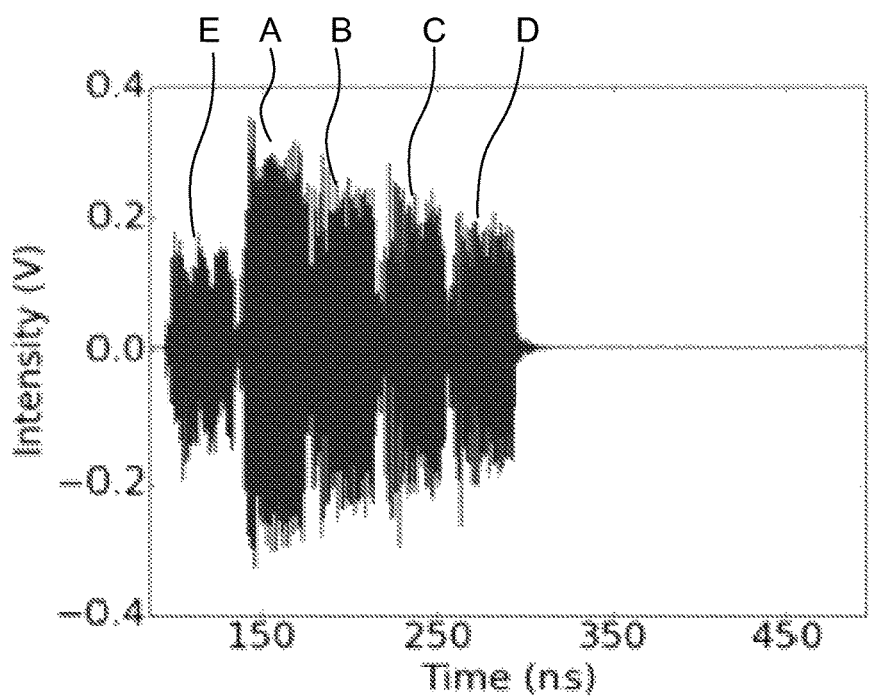
Figure 6A:
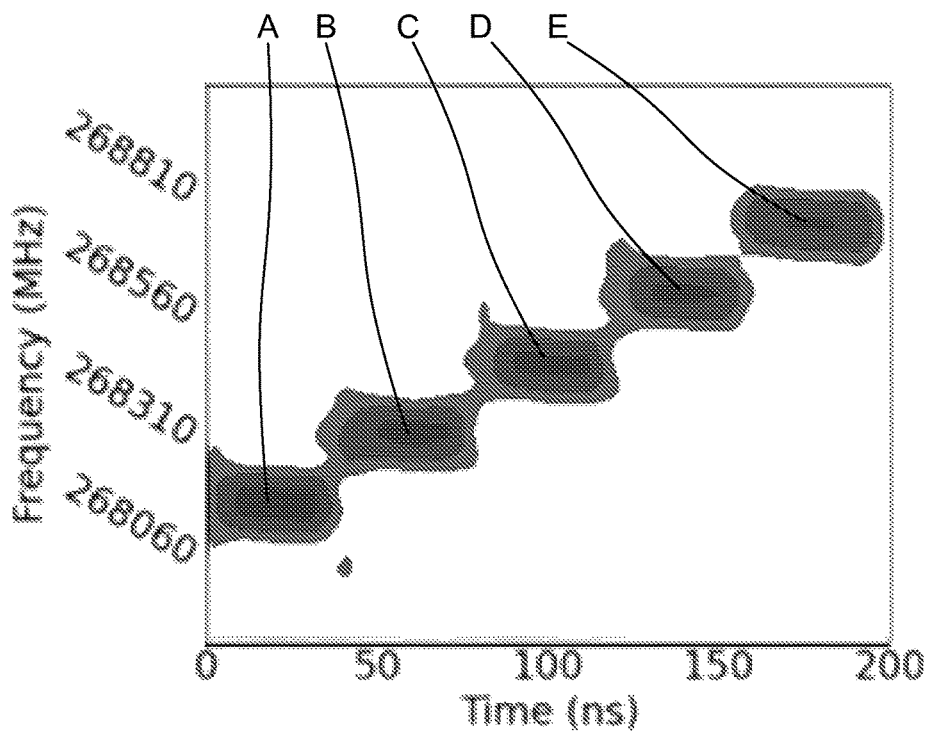
FIGS. 6A and 6B illustrate generally spectrogram plots having frequency on the vertical axis and time on the horizontal access, where an intensity of each permutation of an illustrative excitation sequence is shown generally by the darkened regions, and where the order of the delivered frequencies is varied between the permutations shown in FIGS. 6A and 6B.
Figure 6B:
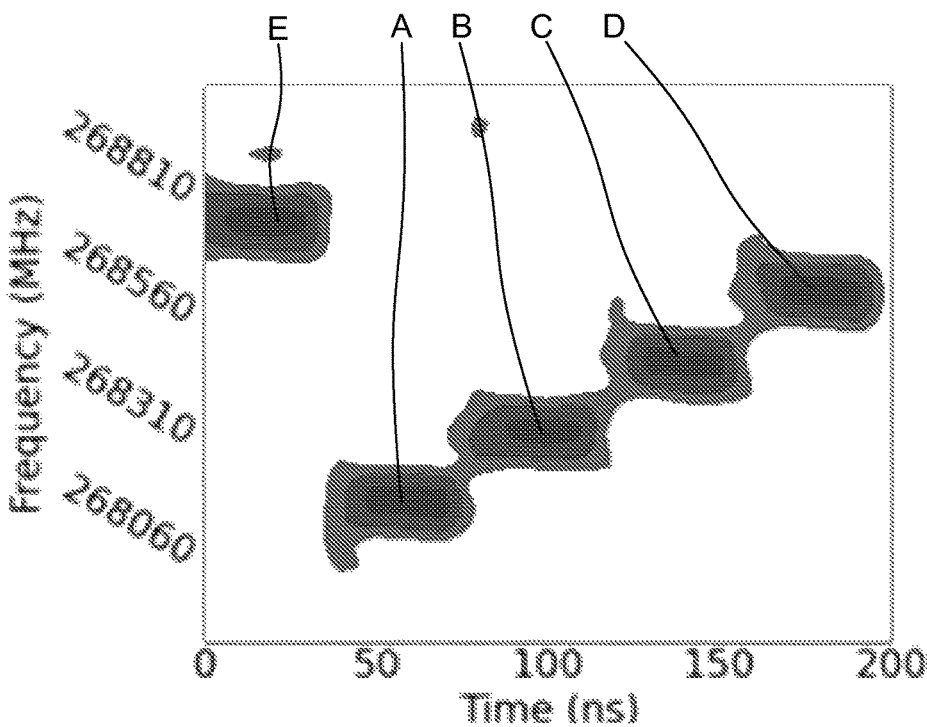
Figure 7A:
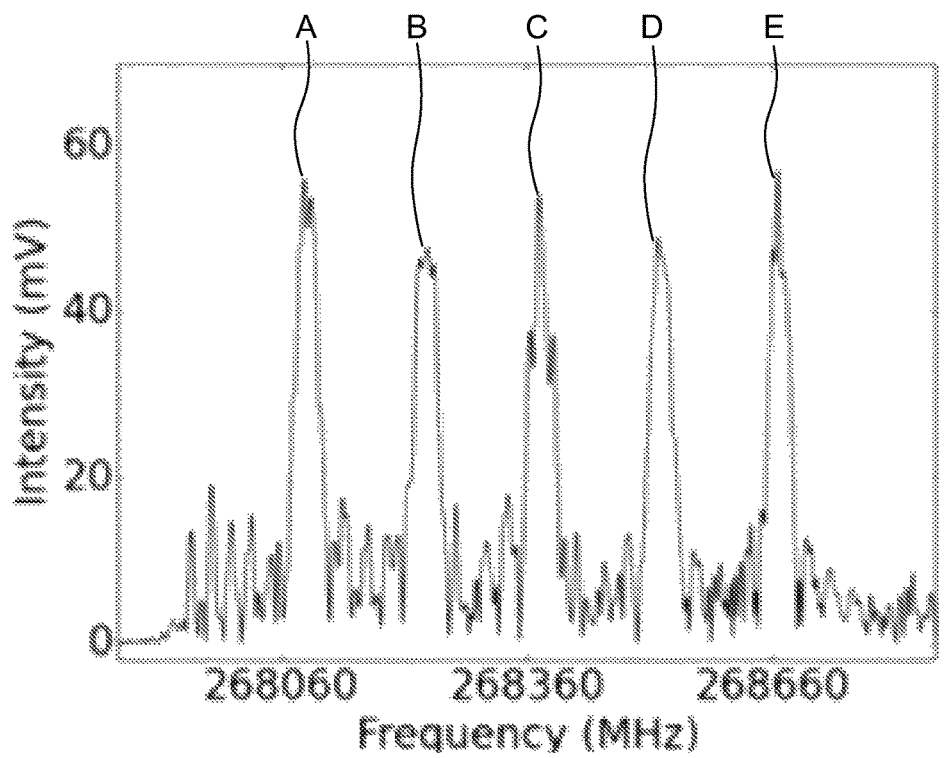
FIGS. 7A and 7B illustrate generally a frequency-domain spectrum that can be obtained numerically by applying a Fast Fourier Transform (FFT) to the time-domain representations shown in FIGS. 5A and 5B to obtain the spectra of FIGS. 7A and 7B, respectively.
Figure 7B:
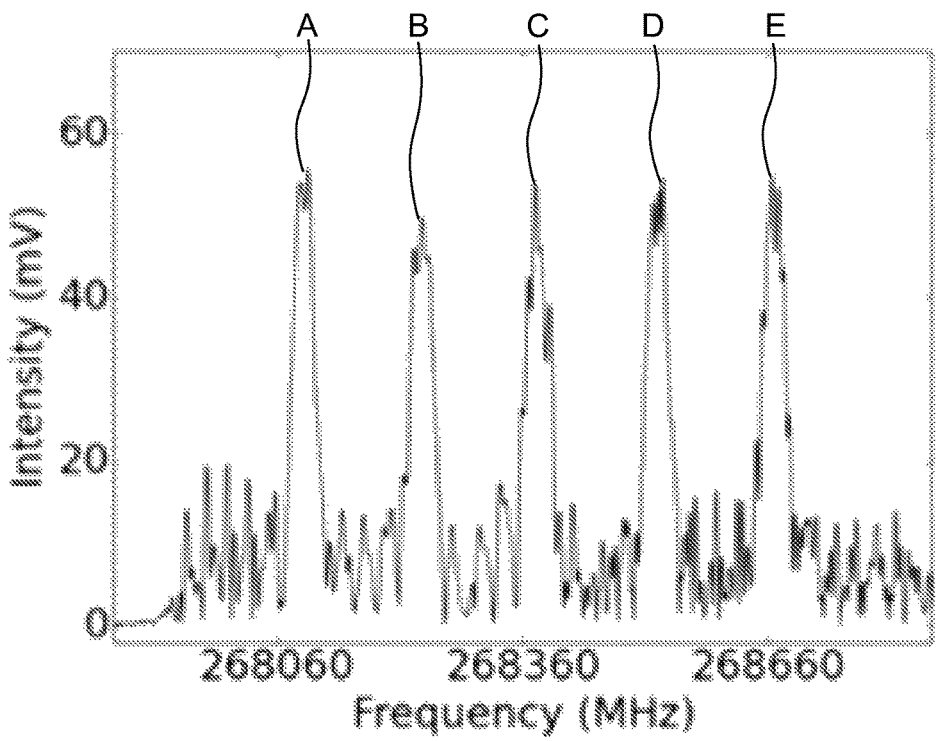

FIGS. 5A and 5B illustrate generally time-domain intensity plots of two illustrative permutations of an excitation sequence, where similar frequencies can be used in each of the sequences shown in FIGS. 5A and 5B, but where the order of the delivered frequencies, A, B, C, D, and E, is varied between the permutations shown in FIG. 5A and FIG. 5B. FIGS. 6A and 6B illustrate generally spectrogram plots having frequency on the vertical axis and time on the horizontal access, where an intensity of each permutation of an illustrative excitation sequence is shown generally by the darkened regions, and where the order of the delivered frequencies, A, B, C, D, and E, is varied between the permutations shown in FIGS. 6A and 6B. FIGS. 7A and 7B illustrate generally a frequency-domain spectrum that can be obtained numerically by applying a Fast Fourier Transform (FFT) to the time-domain representations shown in FIGS. 5A and 5B to obtain the spectra of FIGS. 7A and 7B, respectively, showing peaks corresponding to each of the delivered frequencies, A, B, C, D, and E.

An illustrative example of two pulse sequences is illustrated generally in FIGS. 5A, 5B, 6A, 6B, 7A, and 7B. In this example, the full pulse pattern applies 5 different frequencies back-to-back so that the full "macropulse" duration is about 200 ns—which is within a dephasing time of the sample. In this illustrative example, a full bandwidth excited by the pulse sequence is about 125 MHz (e.g., about 25 MHz for each of the five pulses making up the excitation sequence, with each pulse including a center frequency that can be staggered from the other pulses). Using an approach of delivering short pulses having staggered center frequencies makes it possible to cover 25 times as large a measurement bandwidth compared to a single color pulse with the same 200 ns excitation duration, and such short duration pulses can avoid the non-linearities mentioned above.

Together, FIGS. 5A, 5B, 6A, 6B, 7A, and 7B illustrate generally time and frequency plots of a millimeter wave pulse patter that can be used to excite a gas-phase sample, such as using apparatus or techniques as shown and described elsewhere herein. In the illustration of FIG. 5A, there are five pulses corresponding to frequencies A, B, C, D, and E, delivered serially, each having a square pulse envelope. Each square pulse envelope has a duration of about 40 ns, which provides a corresponding bandwidth in the frequency domain of about 25 MHz for each individual pulse. In FIG. 5B, a second permutation is shown, where frequency E is delivered before frequencies A, B, C, and D. The amplitude slope in the left hand time traces can be attributed at least in part to gain variation in the mm-wave receiver chain.

FIGS. 6A and 6B each illustrate generally a spectrogram which illustrates a time-frequency relationship of two unique permutations of an excitation sequence. In FIGS. 6A and 6B, each pulse has a single corresponding carrier frequency, A, B, C, D, or E, and the pulse are applied sequentially in time as shown illustratively in the time-domain representations of FIGS. 5A and 5B. A sequential application of pulses having single carrier frequencies can be useful when an active multiplier chain (AMC) light source topology is used, because if more than a single input frequency is present at the input of the AMC, the output shows extensive unwanted intermodulation tones.

FIGS. 7A and 7B illustrate generally a numerically-determined Fast Fourier Transform (FFT) of the whole, five pulse sequence for each of two permutations, and show the overall frequency coverage achieved. In this illustration, gain correction (or other normalization) for the receiver amplifiers can be applied in the frequency domain to level the receiver response.

Because a molecular free induction decay signal begins to decay following pulsed excitation, permutation of the colors in the pulse sequence can be used to level transition amplitudes in the spectrum. A set of five permutations, where each color occupies each of the time positions, can be used to provide equal treatment to each individual pulse measurement (e.g., such as by aggregating measurements obtained from each permutation in the frequency domain). The examples of FIGS. 5A, 5B, 6A, 6B, 7A, and 7B illustrate two of a set of five permutations. Many other permutations are possible, and in general a count, N, of individual frequencies can be delivered using a count, M, of permutations, where M is set to be at least equal to N (e.g., to provide at least enough permutations to allow each frequency to occupy each time position across the M permutations).

As an illustration, individual excitation pulse can include spectral bandwidth (e.g., $\Delta v$) that is determined at least in part by its pulse duration (e.g., $t_p$):

$$\Delta v \sim (1/t_p) \quad \text{(EQN. 1)}$$

A total excitation time, T, can be selected to be less in duration than the dephasing time of the macroscopic sample. In this total excitation time, a count, N, of individual pulses that can be applied to the sample can be established using the following relationship:

$$N=(T/t_p) \quad \text{(EQN. 2)}$$

Accordingly, a total bandwidth that can be excited using the FHSS method for a particular combination of pulses can be represented by an approximation:

$$B \sim N \Delta v = (T/(t_p)^2) \quad \text{(EQN. 3)}$$

For a fixed total excitation time (T), the bandwidth, B, excited in the FHSS excitation scheme is generally proportional to $1/(t_p)^2$. In the specific examples described above, moving from a single pulse of duration 200 ns to five separate pulses of duration 40 ns increases the total excitation bandwidth by a factor of 25 reflecting the $(1/(t_p)^2)$ scaling.

Figure 8:
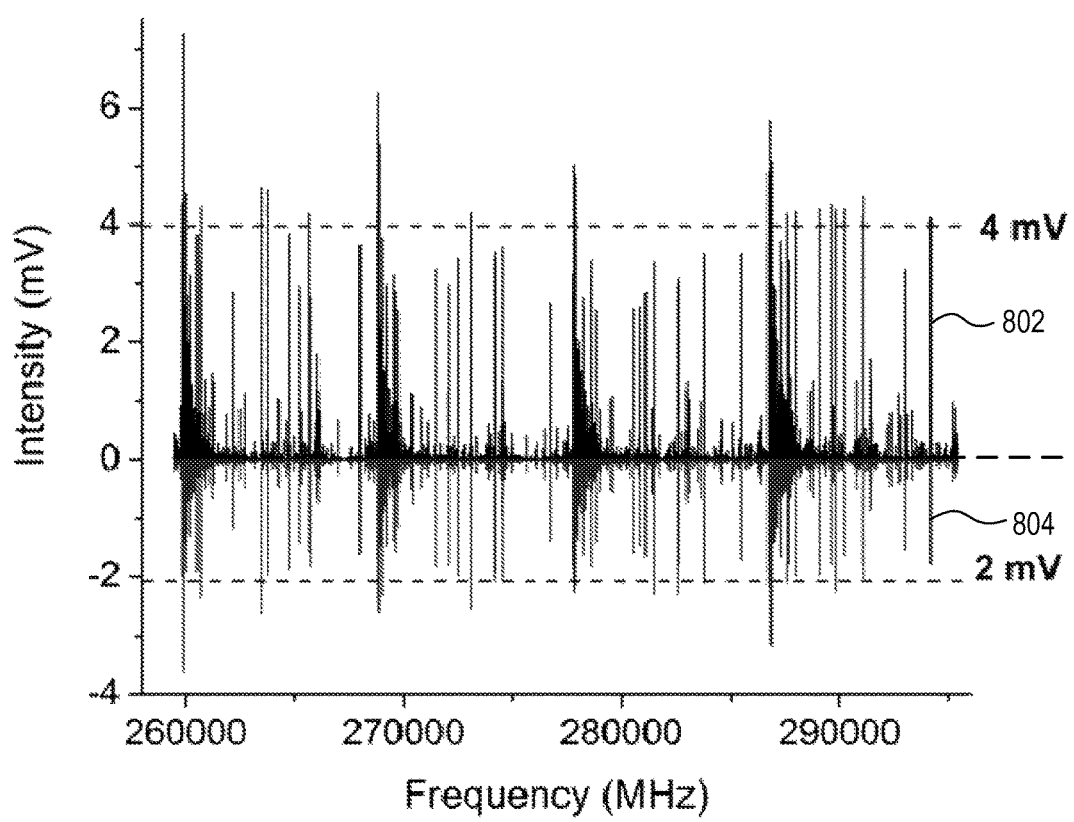
FIG. 8 illustrates generally an illustrative example of a room-temperature rotational spectrum of a 2 milliTorr (mTorr) gas sample of propionitrile using a 65 centimeter (cm) path length, using an FHSS Fourier transform (FHSS-FT) technique, as compared to using a chirped-pulse Fourier transform technique on the same sample.

FIG. 8 illustrates generally an illustrative example of a room-temperature rotational spectrum of a 2 milliTorr (mTorr) gas sample of propionitrile using a 65 centimeter (cm) path length, using an FHSS Fourier transform (FHSS-FT) technique 804, as compared to using a chirped-pulse Fourier transform (CP-FT) technique 802 on the same sample. In both cases, an excitation "macropulse" duration can be about 200 ns. In general, the peak locations indicated using the FHSS-FT technique align well with peak locations established using the CP-FT technique. As mentioned above, an arbitrary waveform generator (AWG) can be used to provide multicolor output in a manner similar to a microwave pulse pattern generator circuit.

Figure 9:
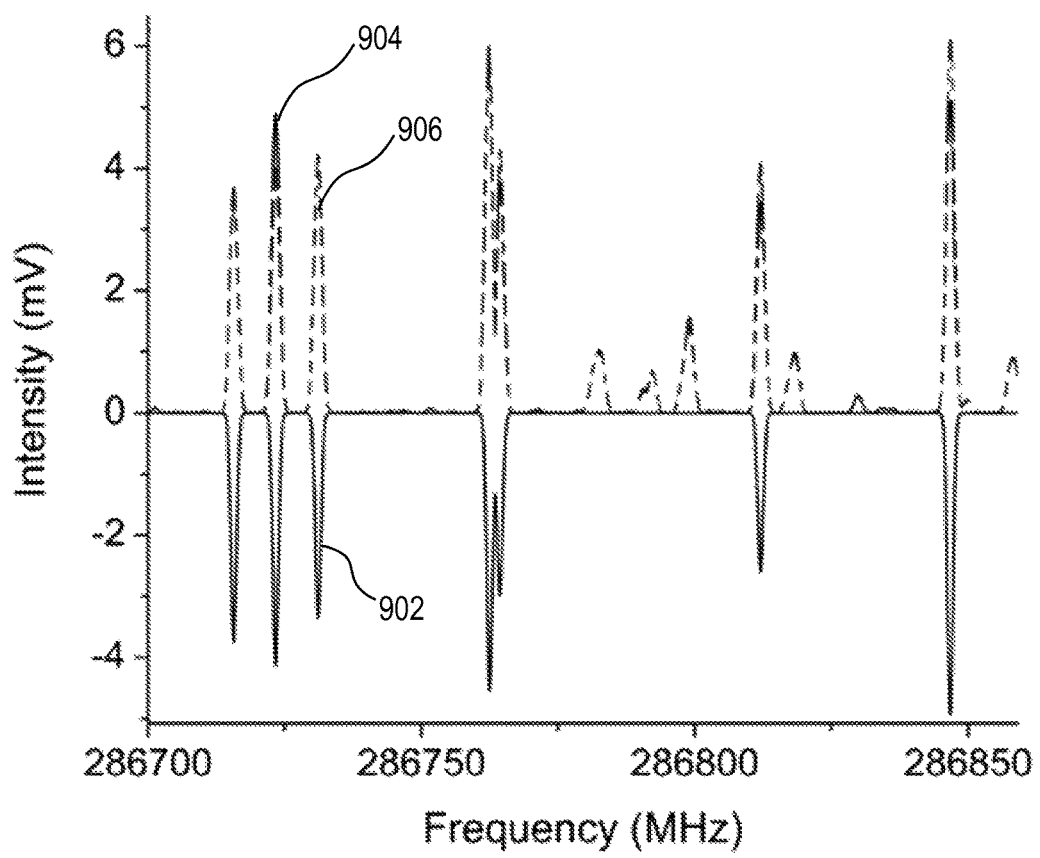
FIG. 9 illustrates generally a further illustrative example of the room-temperature rotational spectrum of a 2 milliTorr (mTorr) gas sample of propionitrile using a 65 centimeter (cm) path length, using an FHSS Fourier transform (FHSS-FT) technique, again as compared to using a chirped-pulse Fourier transform technique on the same sample, and in comparison to a simulation that can be obtained using the NASA Jet Propulsion Laboratory (JPL) database.

FIG. 9 illustrates generally a further illustrative example of the room-temperature rotational spectrum of a 2 milliTorr (mTorr) gas sample of propionitrile using a 65 centimeter (cm) path length, using an FHSS Fourier transform (FHSS-FT) technique 906, again as compared to using a chirped-pulse Fourier transform (CP-FT) technique 904 on the same sample, and in comparison to a simulation that can be obtained using the NASA Jet Propulsion Laboratory (JPL) database 902. Again the peak locations align well when comparing the FHSS-FT and CP-FT techniques, and the largest peak locations align with locations of peaks indicated by the simulation derived from the JPL database 902. The intensity of the resulting spectrum using the CP-FT technique 904 was scaled by a factor of about 1.92.

According to the illustrative examples of FIG. 8 and FIG. 9, the FHSS technique exhibits a measurement sensitivity about a factor of 2 lower than the CP-FT measurement. Without being bound by theory, this result is generally expected because the FHSS method "loses" more of the source power in the spectral wings (e.g., side lobes) of the frequency-domain pulse shape. A practical advantage of FHSS-FT over segmented CP-FT spectroscopy is the potential for significant cost reduction in the microwave components of the excitation source because FHSS need not require use of an AWG.

Figure 10:
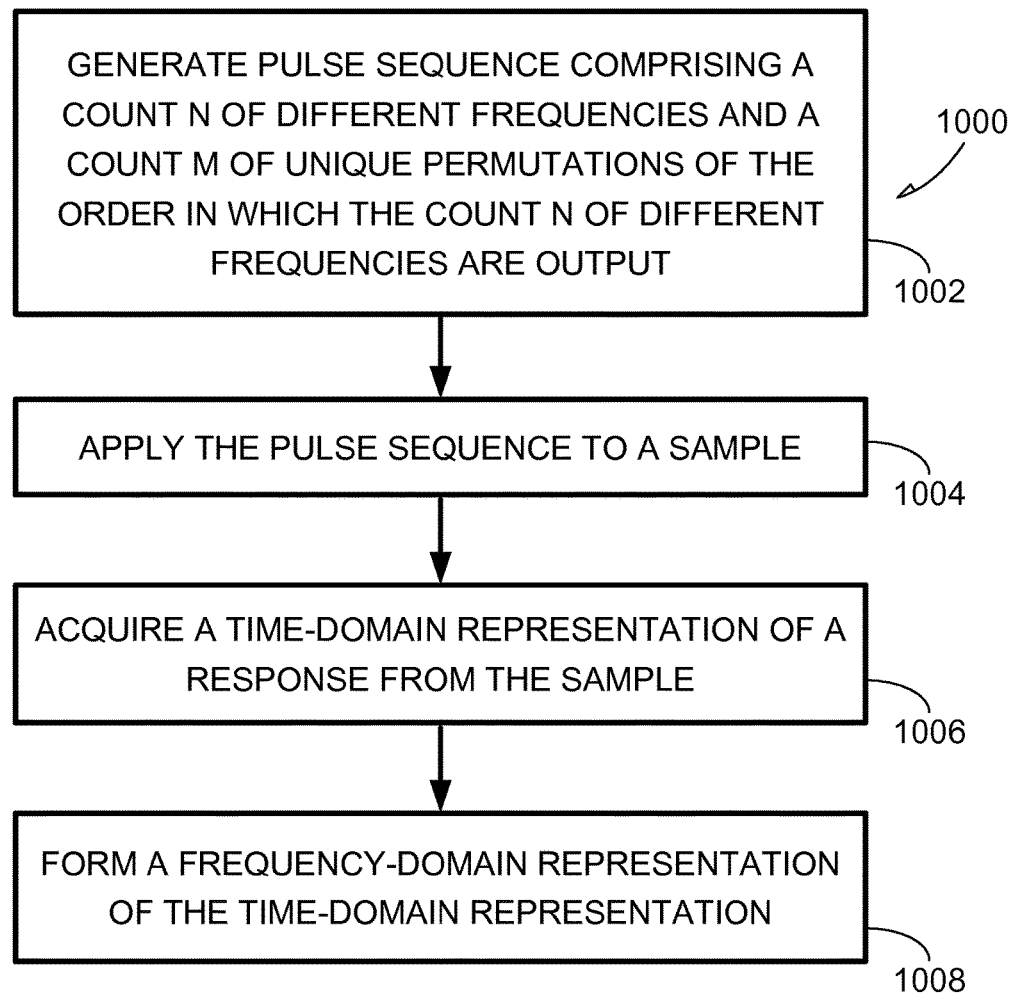
FIG. 10 illustrates generally a technique, such as a method, that can include generating a pulse sequence comprising a count, N, of different frequencies and a count, M, of unique permutations of the order in which the count N of different frequencies are output.

FIG. 10 illustrates generally a technique 1000, such as a method, that can include generating a pulse sequence comprising a count, N, of different frequencies and a count, M, of unique permutations of the order in which the count N of different frequencies are output.

For example, the apparatus of one or more of FIG. 1, 2, 3, or 4 can be used to perform a frequency-hopping spread spectrum spectroscopy technique 1000. The technique 1000 can include, at 1002, generating a pulse sequence comprising a count, N, of different frequencies and a count, M, of unique permutations of the order in which the count N of different frequencies are output. The pulse sequence can be applied to a sample at 1004, such as after upconverting outputs from a pulse pattern generator using one or more of a mixer or a frequency multiplier. In response to applying the pulse sequence to the sample, a time domain representation of a response elicited from the sample can be acquired at 1006, such as using an analog-to-digital converter (e.g., a digitizer). The response elicited from the sample can be detected such as using an antenna or electromagnetic coupler, and placing an output of the antenna or electromagnetic coupler in electromagnetic communication with a mixer (e.g., a sub-harmonic mixer). The resulting analog signal elicited from the sample can thereby be downconverted to a range of frequencies suitable for the analog-to-digital converter.

At 1008, a frequency domain representation of the time-domain representation can be formed, such as using a processor circuit configured to perform a digital discrete transform on the time-domain representation. Such a digital discrete transform can include a discrete Fourier transform, such as a Fast Fourier Transform (FFT).

Figure 11:
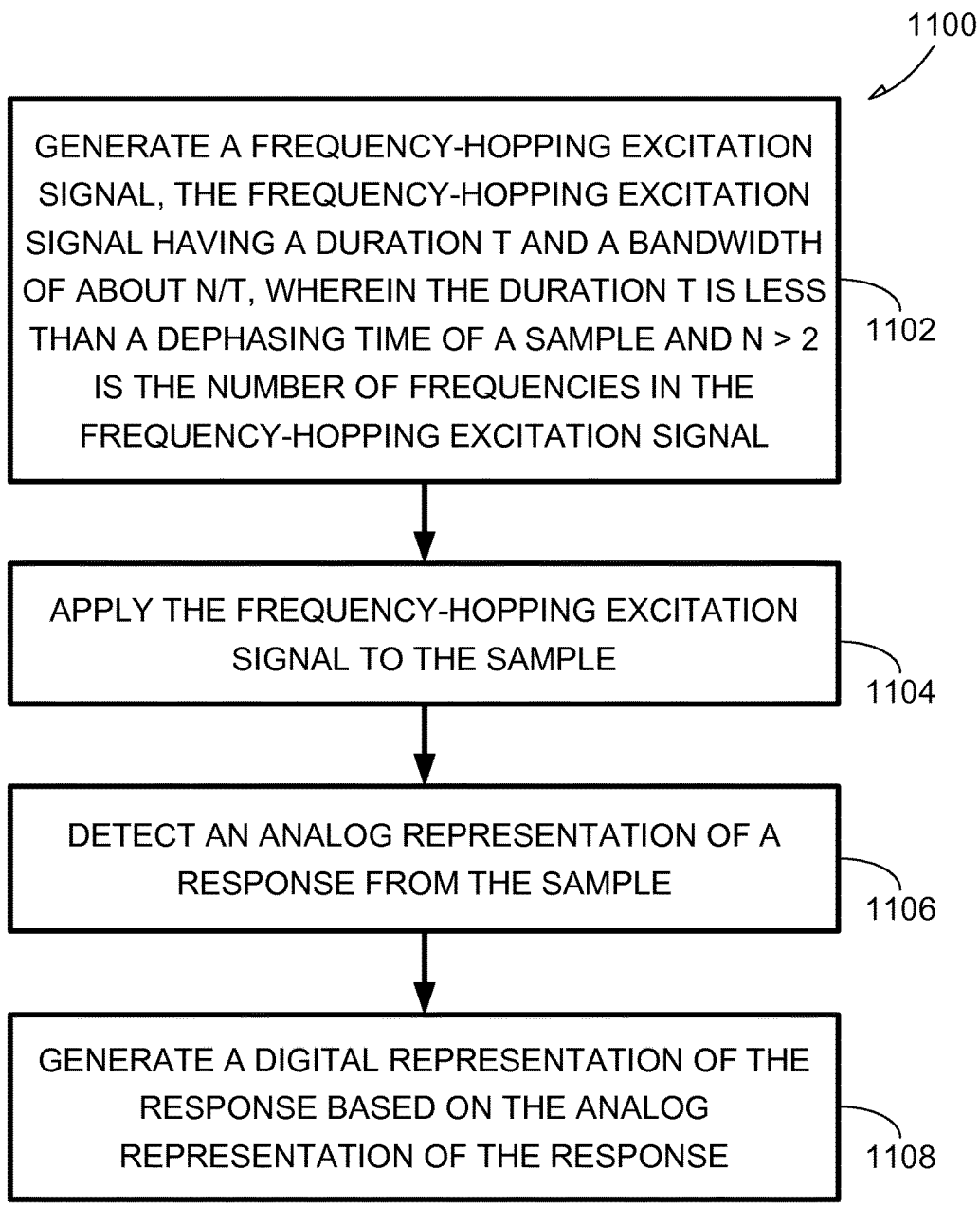
FIG. 11 illustrates generally a technique, such as a method, that can include generating a frequency-hopping excitation signal having a duration, T, and a bandwidth of about N/T, where the duration T is less than a dephasing time of a sample and N>2 is the number of frequencies in the frequency-hopping excitation signal.

FIG. 11 illustrates generally a technique 1100, such as a method, that can include generating a frequency-hopping excitation signal having a duration, T, and a bandwidth of about N/T, where the duration T is less than a dephasing time of a sample and N>2 is the number of frequencies in the frequency-hopping excitation signal. For example, the apparatus of one or more of FIG. 1, 2, 3, or 4 can be used to perform a frequency-hopping spread spectrum spectroscopy technique 1100.

At 1102, a frequency-hopping excitation signal can be generated. The frequency-hopping excitation signal can include a duration, T, and bandwidth of about N/T, wherein the duration T is less than a dephasing time of a sample and N>2 is the number of frequencies in the frequency-hopping excitation signal.

At 1104, the frequency-hopping excitation signal can be applied to a sample, such as after upconverting outputs from a pulse pattern generator using one or more of a mixer or a frequency multiplier. At 1106, an analog representation of a response from the sample can be detected. As mentioned elsewhere herein, a response elicited from the sample can be detected such as using an antenna or other detection scheme, and placing an output of the antenna or electromagnetic coupler in electromagnetic communication with a mixer (e.g., a sub-harmonic mixer). The resulting analog signal elicited from the sample can thereby be downconverted to a range of frequencies suitable for the analog-to-digital converter.

At 1008, a digital representation of the analog representation of the response from the sample can be generated, such as by performing a numerical transformation to obtain frequency-domain information from a time-domain representation of the response.

One or more of the following FHSS approaches can be used according to various examples:

1) A Round-Robin Approach can be Used to Improve the Spectrometer Intensity Response.

A coherent FID signal elicited in the sample starts to decay following each individual excitation pulse (e.g, where the different molecular rotational transitions under the bandwidth of each individual pulse (of different color) are polarized). However, detection of all of the molecular signals generally starts after the last pulse in the sequence. Therefore, signals in the FID elicited by earlier pulses in the excitation sequence have had a longer time to decay and will have suppressed intensity in the Fourier transform analysis. This intensity suppression effect can be reduced or eliminated by performing five measurements that rotate each color through the five time positions. The final spectra can then be averaged or otherwise aggregated (e.g., usually in the frequency domain) to "level" the spectrometer intensity response in relation to each of the excitation colors.

2) Microwave Frequencies can be Chosen to Permit Time-Domain Signal Averaging.

An overall instrument sensitivity can be increased by performing time-domain signal averaging of the FID, such as where relative phases of the excitation pulses are reproducible (e.g., consistent) from measurement cycle to measurement cycle. For example, when using a microwave pulse pattern generator such as illustrated generally in FIG. 2 or 3, phase reproducibility can be achieved by synchronizing or locking all microwave generators to a common frequency reference (e.g., clock) and then choosing frequency intervals having a specified relationship to the measurement time duration. For example, if the full measurement cycle (application of the pulse sequence followed by FID detection) takes 10 microseconds, then the microwave sources will return to their initial phase relationships as long as all frequencies are integer multiples of 100 kHz (e.g., corresponding to a reciprocal of 10 microseconds).

3) The Microwave Pattern Generator can be used for a Range of Coherent Measurements.

The measurement techniques and apparatus described above, such as in relation to FIG. 3, can used to acquire the rotational spectrum in the 260-295 GHz frequency range using a series of microwave pulses. However, the microwave pulse pattern generator circuit can also be used to implement techniques like microwave double-resonance spectroscopy and Hahn echoes that are generally useful for chemical analysis. For example, in double-resonance measurements, a first pulse of the FHSS sequence can be selected to be resonant with a spectroscopic transition in the gas, and the subsequent pulses can be used probe different regions of the spectrum to identify transitions that share a common energy level with the selective excitation pulse.

The microwave pulse pattern generator can also be used for FHSS spectroscopy such as to perform multiplexed Hahn echo experiments where multiple transitions are studied simultaneously. The analysis of the time-dependence of the echo can provide a direct measure of the collisional relaxation rate and can be useful for getting an accurate estimate of the Doppler contribution to the FID decay. An accurate estimate of the Doppler dephasing rate can be translated into an estimate of the molecular mass and can be useful in analyzing unknown chemical species in situ.

VARIOUS NOTES & EXAMPLES

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An apparatus, including:
a pattern generator circuit configured to output a pulse sequence, the pulse sequence including durations during which frequencies selected from a first frequency range are output, including a count N of different frequencies output serially within the pulse sequence, the pulse sequence further comprising a count M of unique permutations of an order in which the count N of different frequencies are output, the count N being at least three;
a frequency multiplier circuit operably coupled to the pattern generator circuit and configured to upconvert the pulse sequence to an upconverted pulse sequence having a higher second range of frequencies beyond the first range of frequencies;
a sample cell in electromagnetic communication with the frequency multiplier circuit and configured to receive the upconverted pulse sequence as an excitation to a sample; and
an analog-to-digital converter configured to acquire a digital representation of an output from the sample cell elicited in response to the upconverted pulse sequence.

2. The apparatus of claim 1, wherein the first frequency range comprises a microwave frequency range; and
wherein the second frequency range comprises a millimeter-wave frequency range.

3. The apparatus of claim 1, wherein the frequency multiplier comprises an active multiplier chain (AMC).

4. The apparatus of claim 1, wherein the pattern generation circuit comprises an integrated digitally-controlled frequency synthesizer circuit.

5. The apparatus of claim 1, wherein the pattern generation circuit comprises a digital-to-analog converter (DAC).

6. The apparatus of claim 1, wherein the analog-to-digital converter is operably coupled to a processor circuit, the processor circuit configured to obtain a frequency domain representation of a time-domain digital representation obtained from the analog-to-digital converter.

7. The apparatus of claim 6, wherein the processor is configured to perform a discrete Fourier transform on the time-domain digital representation so as to yield the frequency domain representation.

8. The apparatus of claim 1, wherein the count M of unique permutations contains a first permutation of the order in which the count N of different frequencies are output and a different second permutation of the order in which the count N of different frequencies are output.

9. The apparatus of claim 1, wherein the count M is equal to N.

10. The apparatus of claim 8, wherein the analog-to-digital converter is coupled to processor circuit, the processor circuit configured to:
obtain respective frequency domain representations of the time-domain outputs elicited by the first and second permutations; and
aggregate the respective frequency domain representations to provide an aggregated frequency domain representation.

11. The apparatus of claim 10, wherein the processor circuit is configured to determine, based on the aggregated frequency domain representation, a central tendency of frequency domain information corresponding to each of the frequencies included in the upconverted pulse sequence.

12. The apparatus of claim 10, wherein the processor circuit is configured to:
determine levels of each of the frequencies in the respective frequency domain representations; and
correct a level of a determined frequency in the aggregated frequency domain representation using information about a difference in determined levels of a respective one of the frequencies included in the first and second permutations.

13. The apparatus of claim 1, wherein the pattern generator circuit comprises respective frequency outputs configured to provide respective ones of the frequencies amongst the count N of frequencies.

14. The apparatus of claim 13, wherein the respective frequency outputs are fixed.

15. The apparatus of claim 13, wherein the respective frequency outputs are adjustable.

16. The apparatus of claim 13, wherein the respective frequency outputs are configured to provide a continuous output.

17. The apparatus of claim 16, wherein the continuous output comprises a sinusoidal continuous wave (CW) output.

18. The apparatus of claim 16, wherein the pattern generator circuit comprises a switching circuit configured to selectively couple a respective one of the respective frequency outputs to a main output of the pattern generator circuit.

19. The apparatus of claim 18, wherein the switching circuit is configured to selectively couple a sequence of respective ones of the respective frequency outputs to the main output to provide the pulse sequence.

* * * * *